*US011071591B2*

(12) United States Patent
Sartor et al.

(10) Patent No.: US 11,071,591 B2
(45) Date of Patent: Jul. 27, 2021

(54) MODELING A COLLAPSED LUNG USING CT DATA

(71) Applicant: COVIDIEN LP, Mansfield, MA (US)

(72) Inventors: Joe D. Sartor, Longmont, CO (US); Arlen K. Ward, Centennial, CO (US); Francesca Rossetto, Longmont, CO (US); Ramesh Raghupathy, New Brighton, MN (US); Srikara V. Peelukhana, Maple Grove, MN (US)

(73) Assignee: COVIDIEN LP, Mansfield, MA (US)

( * ) Notice: Subject to any disclaimer, the term of this patent is extended or adjusted under 35 U.S.C. 154(b) by 355 days.

(21) Appl. No.: 16/045,996

(22) Filed: Jul. 26, 2018

(65) Prior Publication Data
US 2020/0030033 A1 Jan. 30, 2020

(51) Int. Cl.
A61B 34/10 (2016.01)
A61B 5/08 (2006.01)
(Continued)

(52) U.S. Cl.
CPC ............ *A61B 34/10* (2016.02); *A61B 1/0005* (2013.01); *A61B 1/05* (2013.01); *A61B 1/2676* (2013.01);
(Continued)

(58) Field of Classification Search
CPC .............. A61B 6/466; A61B 2034/105; A61B 2090/367; G06T 17/20; G06T 2207/30061
See application file for complete search history.

(56) References Cited

U.S. PATENT DOCUMENTS 6,188,355 B1   2/2001  Gilboa
6,503,195 B1   1/2003  Keller et al.
(Continued)

FOREIGN PATENT DOCUMENTS

DE   102009043523 A1   4/2011
JP   11000309          1/1999
(Continued)

OTHER PUBLICATIONS

"Finite Elements Modeling in Diagnostics of Small Closed Pneumothorax" by J. Lorkowski et al. Advs Exp Med Biol—Neuroscience and Respiration 15:7-13. (Year: 2015).*
(Continued)

Primary Examiner — Jeffrey G Hoekstra
(74) Attorney, Agent, or Firm — Weber Rosselli & Cannon LLP

(57) ABSTRACT

A method of modeling lungs of a patient includes acquiring computed tomography data of a patient's lungs, storing a software application within a memory associated with a computer, the computer having a processor configured to execute the software application, executing the software application to differentiate tissue located within the patient's lung using the acquired CT data, generate a 3-D model of the patient's lungs based on the acquired CT data and the differentiated tissue, apply a material property to each tissue of the differentiated tissue within the generated 3-D model, generate a mesh of the 3-D model of the patient's lungs, calculate a displacement of the patient's lungs in a collapsed state based on the material property applied to the differentiated tissue and the generated mesh of the generated 3-D model, and display a collapsed lung model of the patient's lungs based on the calculated displacement of the patient's lungs.

15 Claims, 8 Drawing Sheets

(51) Int. Cl.

| | | |
|---|---|---|
| *G06T 17/20* | (2006.01) | |
| *A61B 6/03* | (2006.01) | |
| *A61B 6/00* | (2006.01) | |
| *A61B 5/00* | (2006.01) | |
| *A61B 1/05* | (2006.01) | |
| *A61B 1/267* | (2006.01) | |
| *A61B 1/00* | (2006.01) | |
| *G06T 7/00* | (2017.01) | |
| *A61B 90/00* | (2016.01) | |

(52) U.S. Cl.
CPC .......... *A61B 5/0062* (2013.01); *A61B 5/0084* (2013.01); *A61B 5/08* (2013.01); *A61B 6/032* (2013.01); *A61B 6/466* (2013.01); *A61B 6/5247* (2013.01); *G06T 7/0016* (2013.01); *G06T 17/20* (2013.01); *A61B 2034/105* (2016.02); *A61B 2090/367* (2016.02); *G06T 2207/10081* (2013.01); *G06T 2207/30012* (2013.01); *G06T 2207/30061* (2013.01); *G06T 2211/428* (2013.01)

(56) References Cited

U.S. PATENT DOCUMENTS

| | | | |
|---|---|---|---|
| 6,833,814 | B2 | 12/2004 | Gilboa et al. |
| 8,828,023 | B2 | 9/2014 | Neff et al. |
| 9,247,992 | B2 | 2/2016 | Ladtkow et al. |
| 9,259,269 | B2 | 2/2016 | Ladtkow et al. |
| 9,459,770 | B2 | 10/2016 | Baker |
| 9,575,140 | B2 | 2/2017 | Zur |
| 9,770,216 | B2 | 9/2017 | Brown et al. |
| 2003/0095692 | A1 | 5/2003 | Mundy et al. |
| 2003/0164952 | A1 | 9/2003 | Deichmann et al. |
| 2009/0284255 | A1 | 11/2009 | Zur |
| 2011/0085720 | A1 | 4/2011 | Barak et al. |
| 2012/0190923 | A1 | 7/2012 | Kunz et al. |
| 2013/0063434 | A1 | 3/2013 | Miga et al. |
| 2014/0226884 | A1 | 8/2014 | Porikli et al. |
| 2014/0336461 | A1 | 11/2014 | Reiter et al. |
| 2015/0254841 | A1* | 9/2015 | Fujiwara ............... G06T 7/251 378/62 |
| 2015/0265257 | A1 | 9/2015 | Costello et al. |
| 2015/0305706 | A1 | 10/2015 | Kanik et al. |
| 2016/0000302 | A1 | 1/2016 | Brown et al. |
| 2016/0000356 | A1 | 1/2016 | Brown et al. |
| 2016/0005193 | A1 | 1/2016 | Markov et al. |
| 2016/0038248 | A1 | 2/2016 | Bharadwaj et al. |
| 2016/0073854 | A1 | 3/2016 | Zeien |
| 2017/0135760 | A1 | 5/2017 | Girotto et al. |
| 2017/0280970 | A1 | 10/2017 | Sartor et al. |

FOREIGN PATENT DOCUMENTS

| | | |
|---|---|---|
| JP | 2003290131 A | 10/2003 |
| JP | 2005287900 A | 10/2005 |
| JP | 2006204635 A | 8/2006 |
| JP | 2009078133 A | 4/2009 |
| JP | 2010279695 A | 12/2010 |
| JP | 2013506861 A | 2/2013 |
| WO | 0010456 A1 | 3/2000 |
| WO | 0167035 A1 | 9/2001 |
| WO | 2015149040 A1 | 10/2015 |

OTHER PUBLICATIONS

"Lung Mesh Generation to Simulate Breathing Motion with a Finite Element Method" by P-F Villard et al. IEEE Proc 8th Int Conf Information Visualisation. (Year: 2004).*

"A finite element analysis of the effects of the abdomen on regional lung expansion" by S. Ganesan et al. Respiration Physiology. 99. pp. 341-353. (Year: 1995).*

"Computed Tomographic-Based Volumetric Reconstruction of the Pulmonary System in Scoliosis" by C.J. Adam et al. J Pediatr Orthop. Vol. 27, Issue 6. pp. 677-681. (Year: 2007).*

"Lung Lesion Extraction Using a Toboggan Based Growing Automatic Segmentation Approach" by J. Song et al. IEEE Trans Med Imag. vol.35, No. 1. (Year: 2016).*

"Smoothing Lung Segmentation Surfaces in 3D X-ray CT Images using Anatomic Guidance" by S. Ukil et al. Medical Imaging, pp. 1066-1075. (Year: 2004).*

European Search Report dated Aug. 3, 2017 issued in corresponding EP Application No. 17164275.4—1666.

Japanese Office Action dated Mar. 5, 2018 issued in corresponding JP Appln. No. 2017-068088.

Australian Examination Report dated May 25, 2018 in AU Appln. No. 2017202106.

Chinese Office Action dated Jul. 4, 2018 issued in corresponding CN Appln. No. 201710204462.9.

Canadian Office Action dated Jun. 7, 2018 issued in corresponding CA Appln. No. 2,962,695.

PR Web Online Visibility from Vocus, Press Release dated Apr. 10, 2018, "Aether to Launch AI Organ Printing Software," available at http://www.prweb.com/releases/2018/04/prweb15401486.htm [retrieved on Oct. 23, 2018].

PCT Search Report and Written Opinion issued in PCT Application No. PCT/US2019/040265 dated Oct. 25, 2019, 11 pages.

\* cited by examiner

MODELING A COLLAPSED LUNG USING CT DATA

BACKGROUND

Technical Field

The present disclosure relates to surgical systems, and more particularly, to systems and methods for modeling the lungs of a patient using computed tomography (CT) data.

Description of Related Art

As technology has advanced, surgeons have begun to replace classical open surgical techniques with minimally invasive techniques such as laparoscopic and thoracoscopic surgery in an effort to minimize trauma to surrounding tissue, reduce pain, reduce scarring, and reduce the length of time the patient is required to stay in the hospital. Minimally invasive surgery, such as the thoracoscopic approach pioneered in the mid-$19^{th}$ century, involves the use of small incisions (from one to several), typically no larger than 3-10 mm. Originally performed using a cystoscope, advances in medical technology lead to the development of specialized instruments for use in the thoracic cavity, such as a thoracoscope, to view the anatomy within the thoracic cavity while performing the surgical procedure. In the late $20^{th}$ century, Video Assisted Thoracic Surgery (VATS) was developed utilizing a fiber-optic endoscope to further reduce the size of the incisions required to perform the procedure and to provide clearer, more defined images of the thoracic cavity.

Concurrently, advances in medical imaging have enabled clinicians to more accurately depict the anatomy of a patient, and therefore, more accurately identify diseases and the location of any diseased tissue. These advances have enabled clinicians to more efficiently utilize minimally invasive surgical techniques, such as the thoracoscopic approach described above. Using medical imaging, such as CT (including X-ray CT, computerized axial tomography (CAT) scan, positron emission tomography (PET), and single-photon emission CT (SPECT)), a clinician is able to accurately identify lesions or other medical conditions without the need for invasive surgeries (such as an open approach or thoracotomy). Further, three-dimensional reconstructions of organs, anatomical structure, or the like are developed using the images obtained using one of the above noted imaging modalities. Using the three-dimensional model, a clinician is able to segment various tissues from one another and assess an accurate location of the lesion within the thoracic cavity, or in one particular example, within the lungs. This segmentation further enables a clinician to determine the precise tissue segment with its affiliated vessel and bronchial branches and determine the ideal incision level for VATS procedures (such as a segmentectomy, lobectomy, pneumonectomy, or the like). The three-dimensional model and precise identification of the lesion within the lung and its associated vessel and bronchial branches enables clinicians to identify an ideal location for port placement and develop a pathway through which the surgical instruments should be guided during the thoracoscopic procedure. Typically, a fiducial or other marker (e.g., coils or wires) is implanted within the affected tissue using fluoroscopy or other imaging modalities. Thereafter, the location of the fiducial relative to the lesion is checked using imaging and the VATS procedure is performed. However, it is possible for the fiducial to migrate within the tissue, leading to inaccurate identification of the lesion during the VATS procedure, thereby leading to sub-optimal results.

In order to alleviate this issue, image-guided VATS (iVATS) was developed, which incorporates intraoperative imaging (such as fluoroscopy) to help guide the surgical tools to the identified lesion. In this manner, a clinician preoperatively plans the trajectory for the surgical tools (fiducials, forceps, staplers, or the like) and monitors their location within the thoracic cavity using intraoperative imaging.

However, as is typical during a thoracoscopic procedure, it is necessary to deflate a portion of the patient's lungs (i.e., induce atelectasis) in order to provide the requisite space within the thoracic cavity for the surgical tools to be maneuvered. Because VATS and iVATS procedures reconstruct the lung using preoperative imaging modalities, the three-dimensional reconstruction is necessarily of an inflated lung. Therefore, because the patient's lungs are deflated during the procedure, the actual geometry of the patient's lungs has changed relative to the three-dimensional reconstruction, leading to a shift in the location of the lesion within the lungs and thoracic cavity. As a result, the preoperative plan is no longer accurate and the clinician is required to compensate for the altered geometry of the lung during the surgical procedure, extending the length of the procedure and increasing the probability of errors.

SUMMARY

The present disclosure is directed to a system for modeling a collapsed lung of a patient. The method includes acquiring computer tomography (CT) data of a patient's lungs, storing a software application within a memory associated with a computer, the computer having a processor configured to execute the software application, executing the software application to differentiate tissue located within the patient's lung using the acquired CT data, generate a 3-D model of the patient's lungs based on the acquired CT data and the differentiated tissue, apply a material property to each tissue of the differentiated tissue within the generated 3-D model, generate a mesh of the generated 3-D model based on the material property applied to the differentiated tissue and the generated mesh of the generated 3-D model, calculate a displacement of the patient's lungs in a collapsed state, and display a collapsed lung model of the patient's lungs based on the calculated displacement of the patient's lungs.

In a further aspect, differentiating tissue located within the patient's lungs may include grouping similar types of tissue based on a corresponding contrast density associated with the tissue.

In another aspect, differentiating tissue located within the patient's lungs may include identifying low contrast density tissue and high contrast density tissue.

In yet another aspect, identifying low contrast density tissue may include identifying at least one structure from the group consisting of lung parenchyma, pleura fissure lines, and bronchi.

In still another aspect, identifying high contrast density tissue may include identifying at least one structure from the group consisting of luminal structures, hilar structures, and bronchopulmonary lymph nodes.

In another aspect, the method may further include selecting a contrast density tissue from the identified low contrast density tissue and high contrast density tissue and generating an offset shell to represent adjacent structure.

In yet another aspect, the method may further include generating a constraint using an offset shell to create a boundary condition that constrains the calculated displacement of the lung.

In a further aspect, the method may further include applying a directional effect of gravity to the generated 3-D model.

In still another aspect, the method may further include calculating a curvature of the patient's spine in a coronal plane.

In yet another aspect, the method may further include calculating a reduction in lung volume based on the calculated curvature of the patient's spine.

In a further aspect, the method may further include altering the generated 3-D model to reflect the calculated reduction in lung volume.

In another aspect, the method may further include identifying adhesions within a thoracic cavity of the patient and displaying the 3-D model of the patient's lungs as sitting higher in the thoracic cavity of the patient.

In still another aspect, generating a mesh of the generated 3-D model of the patient's lungs may include applying a smoothing algorithm to the 3-D model.

In yet another aspect, the method may further include advancing a surgical instrument within a thoracic cavity of the patient to acquire positional data corresponding to an actual collapsed lung of the patient.

In a further aspect, advancing the surgical instrument within the thoracic cavity may include advancing a surgical instrument having a structured light scanner disposed on a distal portion thereof within the thoracic cavity of the patient, the structured light scanner configured to obtain the positional data of the actual collapsed lung of the patient.

In another aspect, calculating the displacement of the patient's lungs in a collapsed state may include calculating a plurality of displacements of the patient's lungs in a collapsed state, each calculated displacement of the plurality of calculated displacements of the patient's lungs based on a corresponding plurality of lung deflation levels.

In still another aspect, the method may further include selecting a calculated displacement of the plurality of displacements correlating to the positional data obtained by the structured light scanner and displaying a collapsed lung model of the patient's lungs based upon the selected calculated displacement of the patient's lungs.

In yet another aspect, the method may further include recalculating the displacement of the patient's lungs in a collapsed state based on the calculated offset between the first and second fiducials and displaying a regenerated collapsed lung model of the patient's lungs based on the recalculated displacement of the patient's lungs.

In another aspect, advancing the surgical instrument within the thoracic cavity of the patient may include advancing a surgical instrument having a camera disposed on a distal portion thereof configured to display real-time video images of the patient's collapsed lung within the thoracic cavity of the patient, wherein the collapsed lung model is superimposed over the displayed real-time video images of the patient's collapsed lung.

BRIEF DESCRIPTION OF THE DRAWINGS

Various aspects and features of the present disclosure are described hereinbelow with reference to the drawings, wherein.

DETAILED DESCRIPTION

Figure 1:
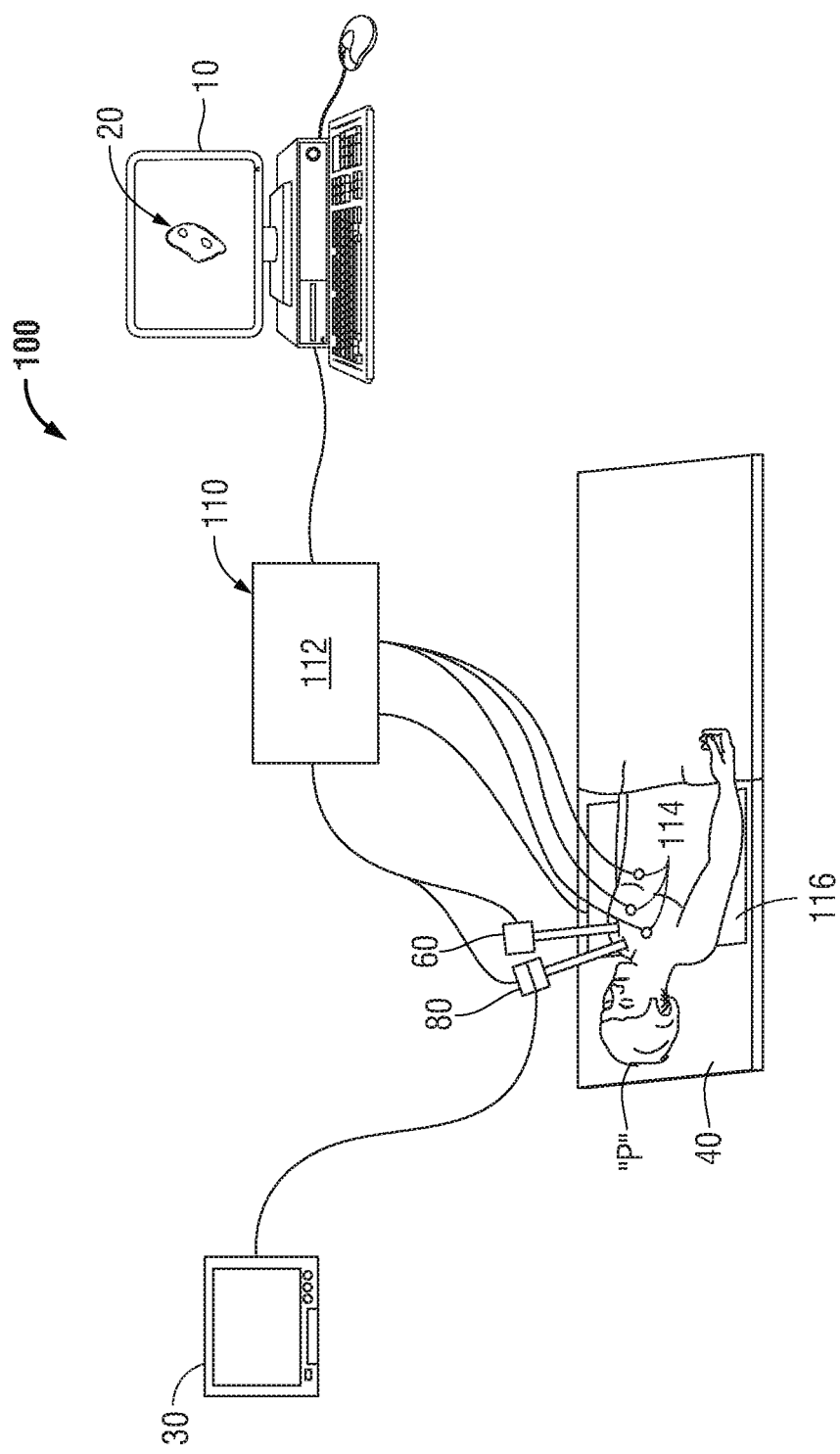
FIG. 1 is a perspective view of a system provided in accordance with the present disclosure configured for modeling a lung and treating an area of interest within the lung.

The present disclosure is directed to methods and systems for modeling the lungs of a patient using computed tomography (CT) data. As described herein, the clinician is able to review CT data of the patient to identify an area of interest illustrating the effects of lung disease. A pathway to the identified area of interest is generated and illustrated on a suitable display of a user interface such that the clinician may use the generated pathway to guide a surgical tool or other device (e.g., an ablation probe, a biopsy device, or the like) to the area of interest and treat the affected tissue. Using the CT data, a 3-D model of the patient's lungs is generated and presented to the clinician via the display. This 3-D model is segmented to define the boundaries of various types of tissue and group together similar types of tissue, such as low contrast density details of the lung (e.g., lung parenchyma, pleura fissure lines, bronchi, and the like) and high contrast density details of the lung (e.g., liminal structures, hilar structures, bronchopulmonary lymph nodes, or the like). The clinician is further able to manually identify the various structures of the lung to complete segmentation of the 3-D model and may confirm that the arteries, veins, and bronchi have been properly differentiated. A smoothing filter is applied to the segmentation of the lung and the 3-D model is reconstructed and displayed in a user interface via the display. In order to most accurately depict the patient's collapsed lung, the 3-D reconstruction is rotated via the user interface to ensure that the patient's lungs appear in the lateral decubitus position (i.e., as if the patient is lying on his or her side), which is the position in which the patient will typically be positioned during the surgical procedure. The curvature of the spine in the coronal or frontal plane is also calculated and utilized to accurately depict the patient's lung volume within the thoracic cavity.

The accuracy of the collapsed model of the lung is also affected by differing material properties, such as elastic modulus, of the low contrast density details and the high contrast density details of the lung. Specifically, the low contrast density details will shrink and/or contract under compression, whereas the high contrast density details tend to maintain their geometry and instead curl or bend. Therefore, the elastic modulus associated with the differentiated structures of the lungs is assigned to ensure that the collapsed model of the lung accurately depicts a real time view of the patient's collapsed lungs. As can be appreciated, in certain instances a nonlinear tissue material response such as hyperelastic model may be assigned to improve the accuracy in representing nonlinear material behavior. Similarly, various other structures located within the thoracic cavity may be identified, such as adhesions, lesions, or the like, and the 3-D model will accommodate these structures by readjusting the model within the thoracic cavity according to the placement of these structures. Gravity also effects how the collapsed lung rests within the thoracic cavity, and therefore, the directional effect of gravity is applied to the 3-D model depending upon the orientation in which the patient is lying on the operating table. Additionally, the degree of tilt of the operating table is also taken into account when applying the directional effect of gravity.

A secondary smoothing algorithm is applied to the 3-D model and thereafter, the 3-D model is meshed in preparation for Finite Element Analysis. Additionally, boundary conditions and loads are applied on the various parts of the model to represent the various attachments and constraints on the lungs, airways, blood vessels. The FEA process is utilized to calculate the displacement of the collapsed lung and ultimately present the collapsed lung model to the clinician via the display. The pathway to the area of interest described above is generated and superimposed on the collapsed lung model such that the clinician may navigate the surgical tool to the area of interest using VATS, iVATS, or any suitable electromagnetic navigation system.

The collapsed model of the lung is superimposed over a real-time view of the patient's lungs such that the clinician may view the various structures within the lung as a thoracoscope and other surgical instruments are navigated within the thoracic cavity and/or lungs. Using the thoracoscope, the clinician compares the collapsed lung model to the real-time view of the patient lungs and can manipulate the collapsed lung model to more accurately reflect the actual volume of the patient's collapsed lung. In this manner, a thoracoscope having a structured light scanner or other suitable device is used to obtain volumetric data of the patient's collapsed lung. This data is utilized to closely match the collapsed lung model to the real-time view of the collapsed lung. The systems and methods of the present disclosure enable a clinician to more accurately treat affected tissue within the patient's lung to reduce the time to complete the surgical procedure and avoid costly clinician errors.

Although the systems and methods detailed herein are generally described with respect to the lungs, it is contemplated that the following systems and methods may be applied to the liver, spleen, or any other organ.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. Although generally described herein as the various determination and/or selection steps being performed by a clinician, it is contemplated that the determination and/or selection steps described herein may be performed by the software application, or a combination of clinician and software application input. As can be appreciated, in certain instances, it may be necessary for the software application to make certain determinations, whereas in other instances it may be necessary for the clinician to make certain determinations. In embodiments, the software application may make a determination and present the determination to the clinician for selection and/or confirmation. In other embodiments, it may be necessary for the software application to provide a prompt or other warning to the clinician regarding the consequences of the clinician's decision, or to provide an alternative selection to the clinician, or combinations thereof. In the following description, well-known functions or constructions are not described in detail to avoid obscuring the present disclosure in unnecessary detail.

As illustrated in FIG. 1, the methods described herein below utilize a system 100 including a navigation system capable of guiding a surgical tool 80 within the thoracic cavity and the patient's "P" lungs "L" to an area of interest "AOI." The navigation system includes a tracking system 110 that is configured for use with the surgical tool 80 and enables monitoring of the position and orientation of a distal portion of the surgical tool 80. The system 100 further includes a computer 10 and a user interface 20 displayed on the display associated with the computer 10 or suitable monitoring equipment 30 (e.g., a video display, FIG. 1). The role and use of the system 100 with the methods described herein will be described in further detail hereinbelow.

Figure 2:
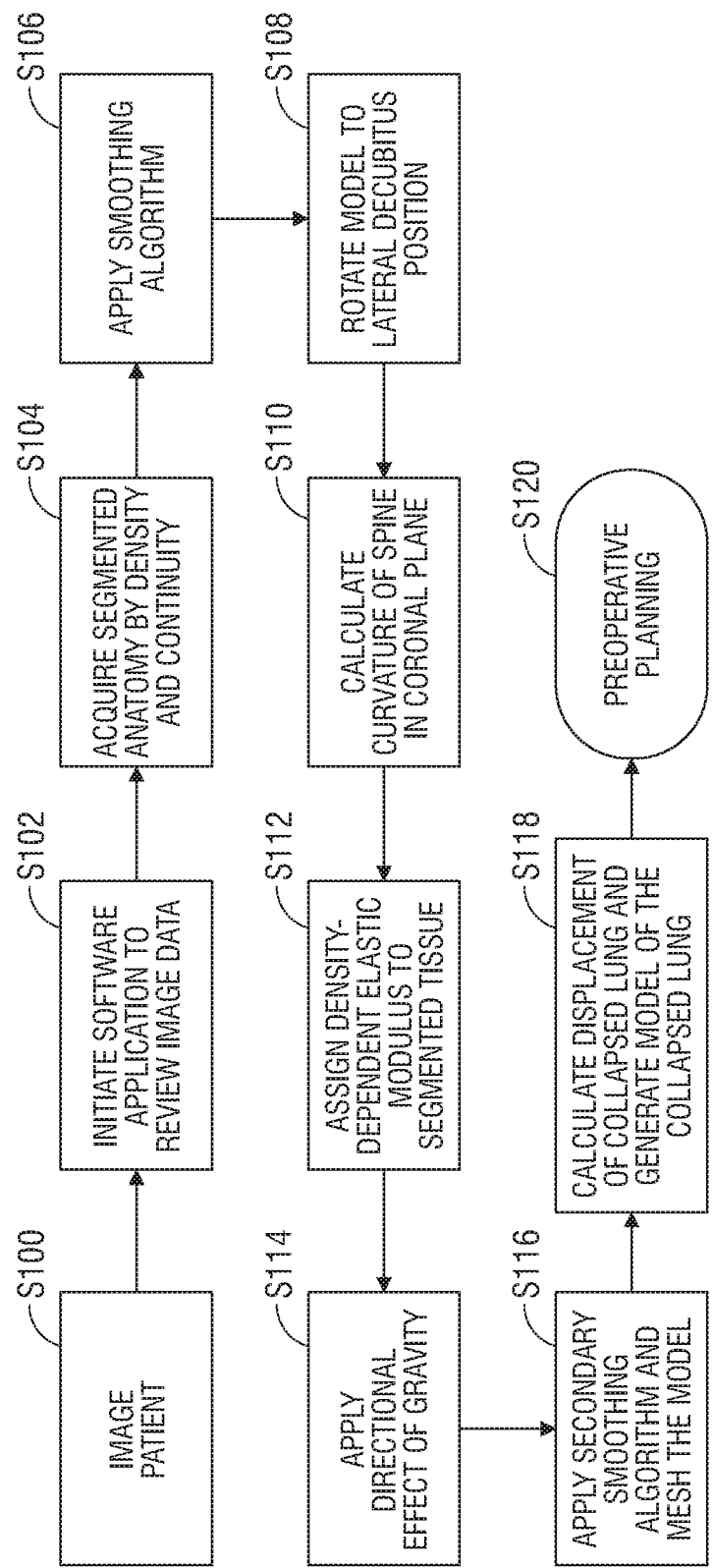
FIG. 2 is a flow chart showing a pre-operative portion of a method of modeling a lung according to the present disclosure.

With reference to the flow chart depicted in FIG. 2, the preoperative portion of a method for modeling the lungs of a patient "P" using CT data is described. Initially, in step S100 the patient "P" is imaged using any suitable CT device (not shown), such as X-ray CT, computerized axial tomography (CAT) scan, positron emission tomography (PET), and single-photon emission CT (SPECT)), and the imaging data is stored within a memory (not shown) coupled to the computer 10 (FIG. 1). The memory may include any non-transitory computer-readable storage media for storing data and/or software that is executable by a processor (not shown), e.g., solid-state, volatile, non-volatile, removable, and non-removable. As can be appreciated, the images may be stored within a memory associated with a remote computer or network (not shown) such as a distributed network or the internet via a wired or wireless connection for the transmission and reception of data to and from other sources.

It is further contemplated that the images may be stored on one or more removable storage devices (not shown), such as optical disks (e.g., blu-ray, DVD, CD, or the like), memory cards (e.g., CompactFlash, Secure Digital, Memory Stick, or the like), Zip disks or Floppy Disks, Disk packs, Magnetic tapes, USB flash drives, external hard drives (e.g., IDE, EIDE, SCSSI, DDS, or the like), or the like.

Following imaging of the patient, in step S102, a software application stored within the memory is executed by a processor associated with the computer to enable review of the image data. One example of such an application is the ILOGIC® planning and navigation suites currently marketed by Medtronic. An area of interest ("AOI;" FIG. 6) illustrating the effects of lung disease (e.g., emphysema, COPD, asthma, cancer, or the like) is identified in the images and its location determined within the lungs "L" of the patient "P." Several methods of identifying an area of interest "AOI" are contemplated such as ultrasound, CT scan, metabolic scanning, or the like. In one non-limiting embodiment, where the patient "P" is not suffering from easily identified lesions or cancers of the lungs, the results of images generated from a previously acquired CT scan can be analyzed to identify areas of hypodensity. Hypodense portions of the lungs "L" are areas where the density of the tissue is less than the surrounding tissue. This may be particularly useful for patients suffering from emphysema as the expanded floppy alveoli or bullae will provide images that have areas which may be substantially darker or blacker than the surrounding tissue, indicating that they are largely air with little to no tissue separating these enlarged alveoli. Because of this hypodensity, image analysis using 3-D image processing is particularly useful as identification of the areas where the densities of the images (measured in Hounsfield units of HU) is below a certain threshold (e.g., 950 HU) approximately the same as air. As will be appreciated, the method of generating a 3-D model described in detail hereinbelow may be utilized to identify the area of interest "AOI." In an alternative embodiment, PET imaging may be utilized to identify areas of low metabolic activity within the lungs "L." As can be appreciated, a device capable of performing a combined PET/CT imaging technique may be utilized, which has proven to be quite accurate. These areas of very little metabolic activity should closely correspond to areas of overinflated alveoli. There is very little metabolic activity in these areas because they are mostly comprised of air. In this way, a PET image set can be utilized to identify the hypodense areas to which navigation and treatment should be directed. After careful analysis, using one of the above described techniques, the location of the area of interest "AOI" within the lungs "L" may be identified and its location stored within the memory coupled to the computer 10 (FIG. 1).

Figure 4C:
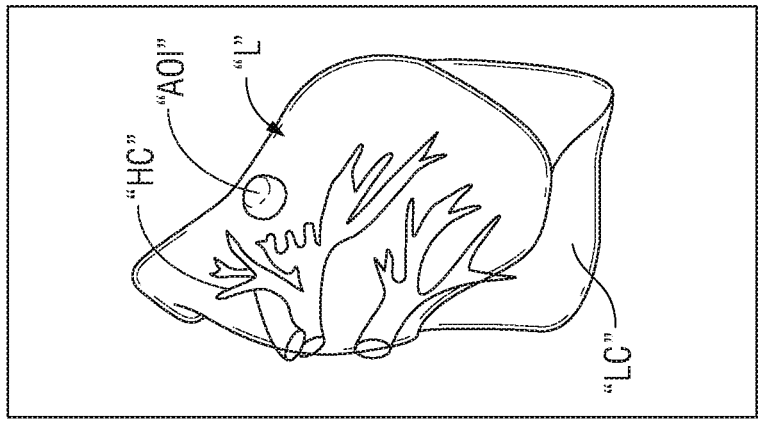
FIG. 4C is a cross-sectional view of a 3-D model of the patient's lungs showing high and low contrast density details that have been partially differentiated.
Figure 4B:
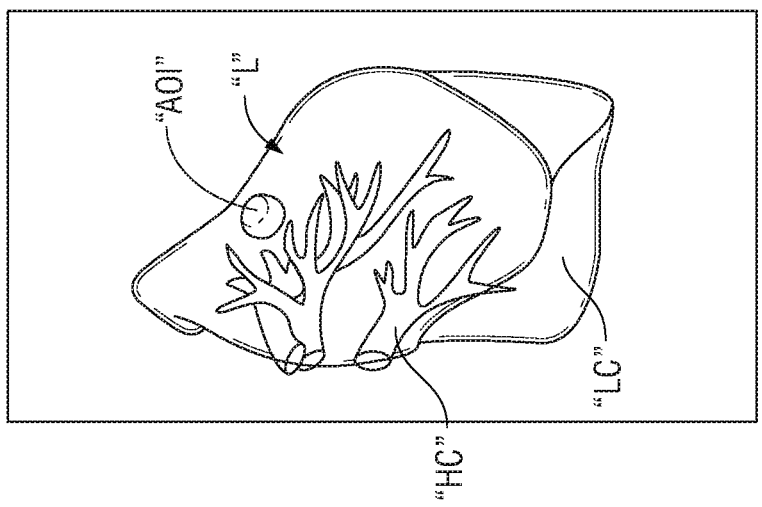
FIG. 4B is a cross-sectional view of a 3-D model of the patient's lungs showing high and low contrast density details that have been differentiated and grouped together.
Figure 4A:
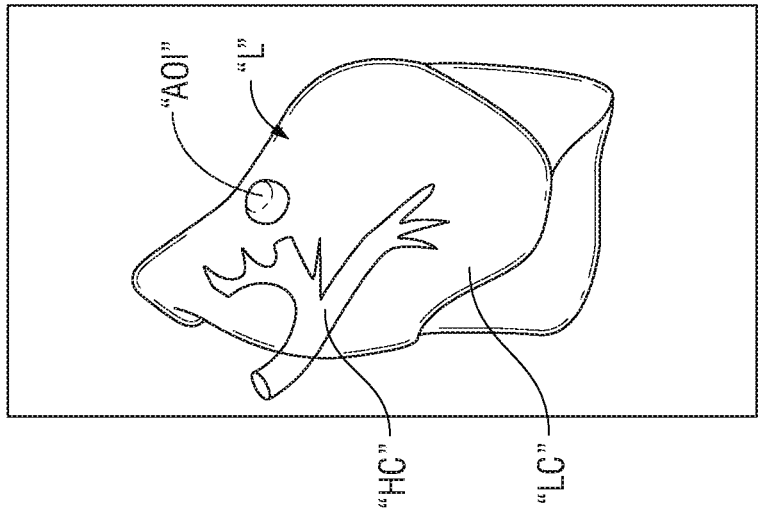
FIG. 4A is a cross-sectional view of a 3-D model of the patient's lung showing an area of interest and high and low contrast density details.

Referring to FIG. 4A, in conjunction with FIG. 2, the image data obtained during step S100 is processed by the software application and a 3-D reconstruction of the CT images is generated using any suitable method known in the art. In one non-limiting embodiment, the 3-D reconstruction is generated using the techniques described in U.S. Patent Application Publication No. 2016/0038248 to Bharadwaj et al. entitled "Treatment Procedure Planning System and Method," filed Aug. 10, 2015, the entire content of which is incorporated by reference herein. In step S104, the software application employs one of a variety of rendering techniques and processing algorithms to isolate, identify, and/or render a generated 3-D volumetric rendering for presentation to the clinician. In this manner, a segmentation algorithm is applied to the 3-D reconstruction to define the boundaries of various types of tissue by comparing the values of each data element of the 3-D reconstruction to a series of thresholds of other similar criteria, such as using density and continuity. As shown in FIG. 4B, the segmentation algorithm groups together similar types of tissue based upon the outcome of the comparison, and in one non-limiting embodiment, may differentiate low contrast density details "LC" of the lung "L" (e.g., lung parenchyma, pleura fissure lines, bronchi, and the like) from high contrast density details "HC" of the lung "L" (e.g., luminal structures, hilar structures, bronchopulmonary lymph nodes, and the like). It is envisioned that the software application may utilize any suitable segmentation algorithm known in the art, such as binary masking, determination of the optimum threshold that separates tissue and background, adaptive region growing, wavefront propagation, automatic or manual determination of seed points in the trachea, liver, or other critical structures, a fill holes algorithm for filling in holes in the binary mask by flood filling the background and inverting the result, a rolling ball algorithm to close the airways, blood vessels, and indentations corresponding to peripheral nodules, and a morphological closing operation. In one non-limiting embodiment, the software application may utilize any of the segmentation techniques described in U.S. Patent Application Publication No. 2016/0038248 to Bharadwaj et al., previously incorporated by reference hereinabove.

Referring to FIG. 4C, in conjunction with FIG. 2, once the software application completes differentiation, it may be necessary for the clinician to confirm that the arteries, veins, and bronchi have been properly differentiated. If the clinician determines that the arteries, veins, and bronchi have not been properly differentiated by the software application, the clinician can select the structure to be differentiated and correct any inaccuracies. Alternatively, it is contemplated that if the software application is unable to differentiate the pulmonary vessels, bronchi, or the like, the undifferentiated pulmonary vessels, bronchi, or the like may be illustrated in the 3-D reconstruction and the clinician may be prompted to perform further artery, vein, and airway differentiation. As can be appreciated, the software application may present each segmented group as a different color or different transparency level that may be selectively adjusted by the clinician in order to enable the clinician to better identify each segmented or differentiated group. It is further contemplated that the software application may illustrate identified structures as opaque and unidentified structures as translucent, or vice versa.

In step S106, the software application applies an image smoothing filter to the segmentation of the lung "L" prior to reconstructing the generated 3-D model of the lung "L". As can be appreciated, the image smoothing filter may be any suitable image smoothing filter known in the art. The software application then reconstructs the 3-D model or representation of the lung "L" using any suitable 3-D rendering process or technique known in the art and displays the 3-D model via the user interface 20 (FIG. 1) portrayed on the display associated with the computer 10 or suitable monitoring equipment 30 (e.g., a video display, FIG. 1). In one non-limiting embodiment, the software application utilizes the processes and techniques described in U.S. Patent Application Publication No. 2016/0038248 to Bharadwaj et al., previously incorporated by reference hereinabove, to generate and display the 3-D rendering of the lungs "L".

As can be appreciated, the patient "P" is typically imaged while lying in the supine decubitus position such that the patient "P" is lying on his or her back. Accordingly, in step S108, the clinician rotates the generated 3-D model to appear in the lateral decubitus position as if the patient "P" is laying on his or her side. This can be accomplished using any suitable user input device such as a mouse, keyboard, or the like (not shown) to click and drag the 3-D model within the user interface 20 (FIG. 1) to the correct position, select a button to automatically rotate the 3-D model to the correct position, toggle up, down, left, right buttons to incrementally rotate the 3-D model in the selected direction, or any other suitable means known in the art. Additionally, it is contemplated that the procedure described hereinabove to manipulate the 3-D model may be utilized to adjust the model to account for the degree of tilt of an operating table 40 on which the patient "P" is lying.

Utilizing the CT data obtained in step S100, the clinician calculates the curvature of the spine in the coronal or frontal plane which is the plane dividing the patient's "P" body into ventral and dorsal sections in step S110 and enters the calculated curvature of the spine into the user interface 20. As can be appreciated, the curvature of the spine in the coronal plane affects lung volume, particularly one side of the thoracic cavity over the other, depending on the direction of the curvature of the spine. It is envisioned that a table or other suitable database containing information correlating spinal curvature to lung volume may be stored in the memory coupled to the computer 10. In this manner, the software application may calculate the reduction in lung volume as a result of the inputted spinal curvature and alter the 3-D model presented to the clinician accordingly. Additionally, the altered lung volume is utilized when generating the compressed lung model, as will be described in further detail hereinbelow.

As can be appreciated, when subjected to compression, the various structures of the lungs "L" deform or compress at differing rates and by differing volumes. In particular, the low contrast density details "LC" (e.g., lung parenchyma, pleura fissure lines and bronchi, and the like) will shrink and/or contract under compression, resulting in a changing of distances between structures in the lung "L". In contrast, the high contrast density details "HC" (e.g., luminal structures, hilar structures, bronchopulmonmary lymph nodes, and the like) will curve or bend but maintain their geometry, thereby remaining within the smaller total volume of the lung "L" resulting from the applied compression. This variance amongst the different structures within the lung "L" is a result of density-dependent material properties, such as a density-dependent elastic modulus (e.g., Young's modulus) associated with each structure. To account for differences in elasticity, the clinician assigns each identified volume an elastic modulus in step S112, which is utilized by the software application when calculating the deformed model of the lung "L." As can be appreciated, additional properties, such as Poisson's ratio or the like, may be assigned to the differentiated structures, and in particular, to the lung parenchyma, which has a variable compressibility stemming from removal of air during the deflation of the lung "L." In an instance where the loss of the air mass within the lung parenchyma is considered to be insignificant, the clinician may opt to assign the lung parenchyma its density dependent elasticity and compressibility via the user interface 20. Alternatively, where the loss of the air mass is considered to affect the elasticity of the lung parenchyma, the software may adjust the density dependent elasticity and compressibility of the lung parenchyma via the user interface 20 in order to best match the actual lung displacement, attained either by optical surface imaging/mapping or by best fit as identified by the clinician.

It is envisioned that additional structures within the thoracic cavity can be identified in the 3-D model, such as adhesions "A," lesions, or the like. Specifically, any adhesions "A" that may be present may be recognized by the software application via the CT data. Alternatively, it is contemplated that the clinician may manually add or identify adhesions "A" via the user interface 20. In embodiments, the software application may account for adhesion "A" presence by forcing the lung "L" to sit higher in the thoracic cavity, by fixing the adhesions "A" to the fixed boundary at the ribcage and applying elastic models to determine displacement, or combinations thereof. Conversely, the software application may recognize the removal of adhesions "A," or the removal of the adhesions "A" may be manually entered into the software application by the clinician, and the software application will readjust the model accordingly (e.g., the lung "L" will sit further down towards the hilum). The software application can also assign higher or lower elastic properties to non-structural portions of the pre-deflation lung volume based on the CT data or by manual input by the clinician. In this manner, tumor (or other lesion) volumes can be assigned a more rigid behavior (e.g., less prone to being compressed) and the displacement of the model will be recalculated accordingly, as will be described in further detail hereinbelow. Additionally, it is contemplated that the software application may use information from patient electronic medical records (EMR) to estimate a more likely level of lung deflation as the elastic properties of the lung tissues will be affected by common lung conditions such as chronic obstruction pulmonary disorder (COPD). As can be appreciated, the patient EMR may be accessed by the software application using any suitable means, such as via the memory coupled to the computer 10 (FIG. 1), removable storage devices, such as those described hereinabove, via a remote computer or network such as a distributed network or the internet via a wired or wireless connection.

In step S114, the clinician applies the directional effect of gravity on the 3-D model. It is envisioned that any suitable algorithm or means for applying the directional effect of gravity known in the art may be utilized. As can be appreciated, the orientation of the 3-D model within the user interface 20 (FIG. 1) must be known in order to accurately apply the directional effect of gravity. Accordingly, if the clinician has already rotated the 3-D model to appear in the lateral decubitus position, as described hereinabove, the directional effect of gravity will be applied to the 3-D model such that the gravitational force acts in a lateral direction with respect to the 3-D model. It is envisioned that once the directional effect of gravity has been applied to the 3-D model, as the clinician rotates the 3-D model within the user interface 20, the direction of the gravitational force will readjust with respect to the 3-D model to ensure that the gravitational force is acting upon the 3-D model in the correct direction. Additionally, as noted above, the operating table 40 (FIG. 1) may be tilted during the procedure. Accordingly, it is contemplated that degree of tilt of the operating table 40 may be accounted for in the 3-D model such that the directional effect of gravity acts upon the 3-D model in the correct direction.

Once the 3-D model is generated and segmentation has been completed, in step S116, the software application applies a secondary smoothing algorithm to prepare the 3-D model for meshing. As can be appreciated, a 3-D model having rough edges which may give rise to malformed elements (e.g., edge inversion, concave elements, or the like), results in an inaccurate solution or needlessly complex mesh solutions. The secondary smoothing algorithm ensures that the generated mesh that is valid. It is contemplated that the secondary smoothing algorithm may be any suitable smoothing algorithm known in the art capable of smoothing a 3-D model in preparation for meshing the model for Finite Element Analysis (FEA).

Figure 6:
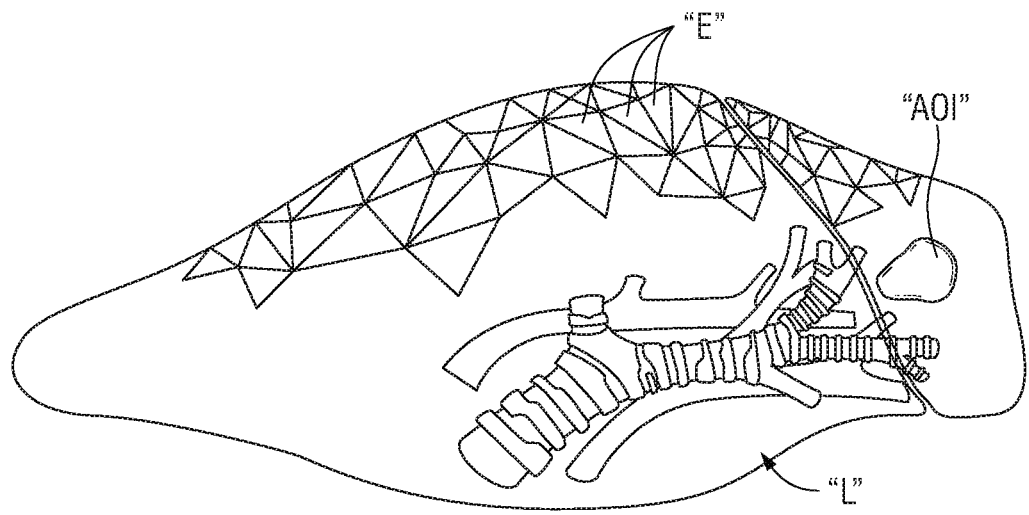
FIG. 6 is a cross-sectional view of a 3-D model of the patient's lungs showing the model having a generated mesh applied thereto.

After completion of the secondary smoothing algorithm, the 3-D model is meshed (See FIG. 6). Initially, the clinician determines the size of the elements "E" to be generated during the meshing process. It is contemplated that the size of the elements "E" may be entered into the user interface 20 (FIG. 1) manually by the clinician or may be selected automatically by the software application. As can be appreciated, the size of the elements "E" will affect the accuracy of the model of the compressed lungs and will depend on the nature of the procedure being performed, the processing power available, and/or the time allotted to generate the mesh and process the results. In this manner, it is envisioned that the mesh may be generated using one or more computers that are coupled to computer 10 (FIG. 1), using techniques such as clustering, parallel computing, massively parallel computing, grid computing, or the like. It is further envisioned that the clinician may assign different element "E" sizes to various portions of the lung "L." In this manner, smaller or finer elements "E" may be selected for the portions of the lung "L" that are more readily affected by lung compression, such as lung parenchyma or other critical structures, and larger or coarser elements "E" may be selected for portions of the lung "L" that are less likely to be affected by lung compression. In this manner, the clinician may optimize the model given the available resources or the needs of the procedure being performed.

Additionally, the clinician may select the type of element "E" to be used in the mesh, such as tetrahedral, hexahedral, mixed-element, combinations thereof, or any other suitable element "E" type known in the art. It is further contemplated that the clinician may assign different mesh types to different segments of the lung "L," depending on the type of tissue and the geometry of the segment. Alternatively, it is contemplated that the software application may automatically assign the element "E" type to be used during the generation of the mesh depending on the computing power available and the needs of the procedure being performed. It is envisioned that the 3-D mesh may be generated using any suitable technique known in the art, such as the marching cubes technique, the advancing front technique, the red green tetrahedral technique, marching cubes with Delaunay-based meshes, variational tetrahedral meshing, hexahedral meshes, mesh adaptation techniques such as the mesh-matching algorithm, meshing 4-D domains, mesh warping, and the like. It is envisioned that any suitable segmentation and meshing program may be utilized to generate the meshing, such as those marketed and sold by Materialize NV, such as Mimics or 3matic. In embodiments, segmentation and meshing may be completed using the Emprint™ ablation system or superDimension™ navigation system marketed and sold by Medtronic.

It is envisioned that simplification of the representation of structures and organs surrounding the patient's lungs may be performed for modeling the displacement and motion of the lungs in the collapsed state. It is contemplated that additional geometries may be created by translating and offsetting (dilation or contraction) existing geometries to provide boundary constraints on the lungs. For instance, the surface of the lung parenchyma may be expanded to create an offset shell surface that can be used to provide an envelope within which the lung has to reside during the collapse. In embodiments, other structures or organs (e.g., parenchyma, pleura, hilar, mediastinum, heart, etc.) may be represented by selecting a low contrast density or high contrast density tissue and creating an offset shell or envelope. Additionally, it is contemplated that boundary conditions that fully or partially constrain the density of the lung or adjacent tissue (e.g., pleura, the diaphragm, hilar structures, the heart, the chest wall, etc.) can be assigned by creating offset shells or envelopes. It is further contemplated that contact between the parenchyma and the organs and structures surrounding the lungs can be reduced to only contact between the lung and the offset shell envelope. It is envisioned that further refinement may be added to the offset shell representation by treating the offset shell representation as a rigid structure or specifying stiffnesses (or elasticities) in different regions corresponding to the modulus of the neighboring tissue. Additionally, differential pressure loads may be applied on various surfaces (lung parenchyma, airways, etc.) and the collapse of the lung is solved by Finite Element Analysis.

The resulting meshed 3-D model forms a Computational Lung Model (CLM), which is the 3-D model that is displayed to the clinician on the display associated with the computer 10 or the monitoring equipment 30 (FIG. 1) during the surgical procedure, as will be described in further detail hereinbelow.

Figure 7:
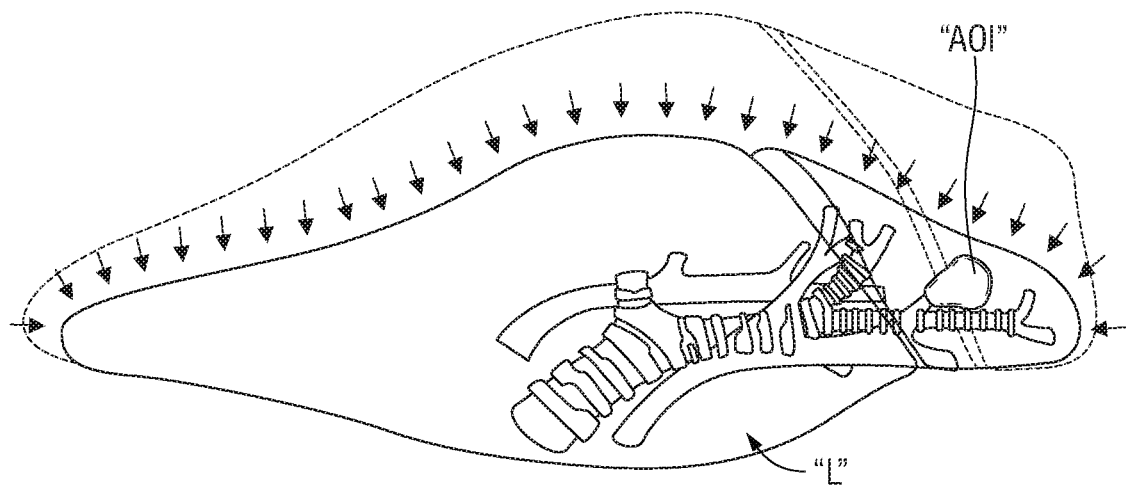
FIG. 7 is a cross-sectional view of a 3-D model of the patient's lungs showing the lungs in a collapsed state.

In step S118, the displacement of the collapsed lung "L" is calculated (See FIG. 7). It is contemplated that any suitable model may be employed to calculate the displacement of the collapsed lung, such as a linear elastic model or a hyperelastic model such as the Saint Venant-Kirchhoff model, the Fung model, or the Mooney-Rivlin model, although other suitable hyperelastic models may also be employed. As can be appreciated, the type of displacement model employed may be selected depending upon the type of tissue being analyzed.

It is contemplated that the clinician may select a desired level of lung deflation depending upon his/her experience and/or interpretation of the patient's condition. The clinician may either increase or decrease the amount of lung deflation such that the predicted model may more closely resemble observed conditions. As can be appreciated, a series of solutions using a variety of loading and material arrangements may be calculated by the system depending on the computation load, mesh size requirements, and available computational power. By calculating several solutions, the clinician is able to select the solution that most closely matches the patient "P" at the time the procedure. At this point, the preoperative constructs of the CLM are complete and in step S120, the clinician proceeds to preoperative planning utilizing the CLM generated as a result of the procedure described hereinabove.

Figure 12:
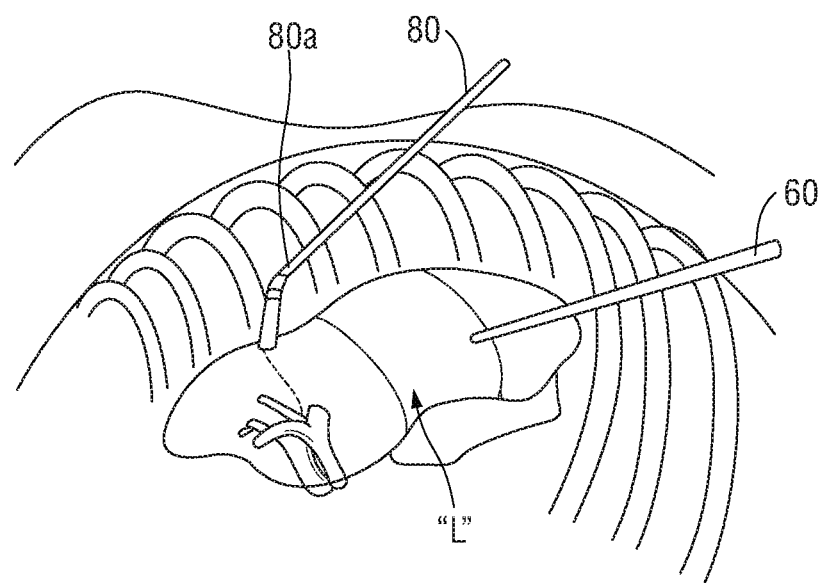
FIG. 12 is a cross-sectional view of the patient's thoracic cavity showing a surgical tool and the thoracoscope of FIG. 9 advanced therein.

During preoperative planning, the clinician utilizes the software application to determine a pathway through which the surgical tools used to treat the area of interest "AOI" may be advanced within the patient "P." Additionally, the software application may identify an optimal location at which a trocar or port may be introduced to most easily reach the area of interest "AOI" using a surgical tool 80, as shown in FIG. 12. This pathway is illustrated on the display associated with the computer 10 or the monitoring equipment 30 (FIG. 1) and the progress of the surgical tool 80 may be monitored by the clinician as the surgical tool 80 is advanced within the thoracic cavity and/or lungs "L" of the patient "P." As can be appreciated, the pathway may be superimposed on video images captured by a suitable VATS or iVATS thoracoscope, or any other suitable device capable of being advanced within a patient "P" and capture video images, such as a laparoscope, endoscope, or the like. It is envisioned that any suitable software application capable of generating a pathway to the area of interest "AOI" may be utilized, and in one non-limiting embodiment, the ILOGIC® planning and navigation suites currently marketed by Medtronic are utilized. It is further contemplated that an electromagnetic navigation system may be utilized to monitor the location of the surgical tool 80 within the patient "P," as will be described in further detail hereinbelow.

Figure 3:
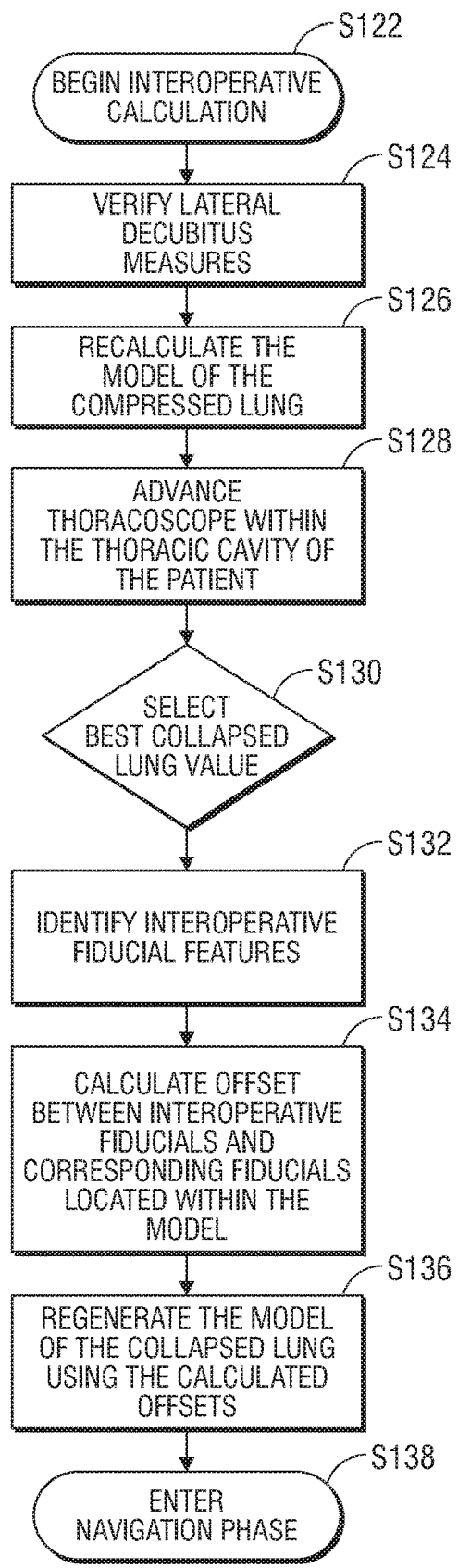
FIG. 3 is a flow chart showing an intraoperative portion of the method of modeling a lung according to the present disclosure.

Referring now to the flow chart depicted in FIG. 3, after preoperative planning is complete, the procedure begins in step S122 and intraoperative calculations are performed to most accurately model the collapsed lung. Initially, in step S124, the clinician verifies the lateral decubitus defining measures to ensure that the orientation of the CLM accurately reflects the real-time position of the patient's "P" lungs "L." It is contemplated that the clinician may manipulate the position of the patient "P" to align the position of the lungs "L" with that of the CLM, or alternatively, the clinician may select the CLM within the user interface 20 (FIG. 1) and drag the CLM to a position that most accurately reflects the real-time position of the patient's "P" lungs "L."

As can be appreciated, if the clinician manipulated the orientation of the CLM within the user interface 20 (FIG. 1), the gravitational effect will act upon the lungs "L" in a different direction than which was originally applied. Accordingly, once the position of the CLM and the real-time position of the patient's "P" lungs "L" are accurately correlated, in step S126, the CLM is recalculated to ensure that displacement of the lungs "L" most accurately reflects the directional effect of gravity. As can be appreciated, the angle of the operating table 40 (FIG. 1) may also be entered (e.g., via the user interface 20) and the model is regenerated by the software application to correctly apply the directional effect of gravity on the model based upon the angle of the operating table 40.

Figure 8:
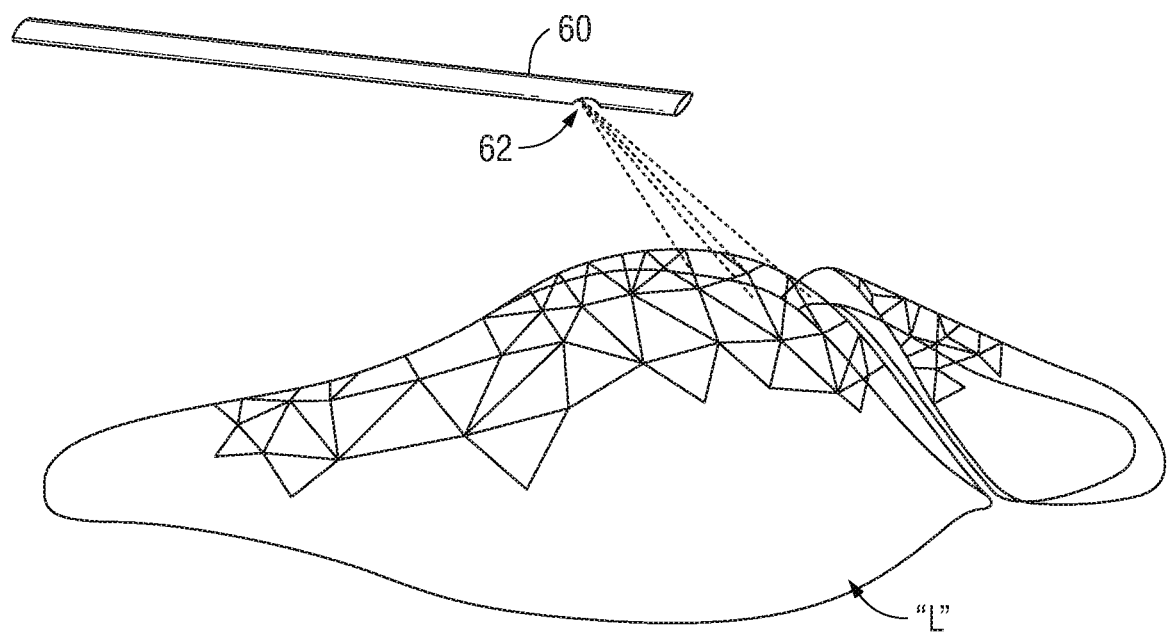
FIG. 8 is a cross-sectional view of a patient's thoracic cavity showing a thoracoscope advanced therein and the 3-D model superimposed over a real-time view of the patient's lungs.

In step S128 the clinician may advance a thoracoscope 60 (FIGS. 8-10) or other suitable device, such as an endoscope or laparoscope, within the thoracic cavity of a patient "P". It is contemplated that the thoracoscope 60 may include any suitable structured light scanner 62 (FIG. 9) known in the art, such as an LED or LED infrared laser that is disposed in to a scan patter (line, mesh or dots), by rotating mirror, beam splitter, or diffraction grating. In one non-limiting embodiment, the structured light scanner 62 is an LED laser having collimated light. The thoracoscope 60 further includes an IR camera 64 (FIG. 9) disposed thereon that is capable of detecting IR light. It is contemplated that the IR camera 64 may be any thermographic camera known in the art, such as ferroelectric, silicon microbolometer, or uncooled focal plane array (UFPA). It is further contemplated that the various sensors disposed on the thoracoscope 60 may be separate and distinct components with associated hardware and/or software, or may be part of a commercial platform such as Intel®'s RealSense™. For a detailed description of an exemplary thoracoscope or endoscope having a structure light scanner, reference may be made to U.S. Provisional Patent Application No. 62/154,958 filed Mar. 31, 2016, entitled THORACIC ENDOSCOPE FOR SURFACE SCANNING to Sartor et al., the entire content of which is incorporated herein by reference.

Figure 5:
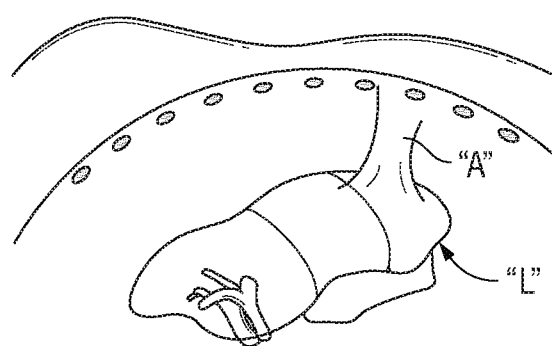
FIG. 5 is a cross-sectional view of a 3-D model of the patient's thoracic cavity showing the lungs and adhesions attached thereto.

If several solutions for the CLM are calculated in step S118 (detailed hereinabove), using the positional data obtained by the structured light scanner 62 (FIG. 9), the clinician selects the CLM solution (e.g., collapsed lung volume) that most accurately reflects the observed collapsed volume of the patient's lungs "L" in step S130. Additionally, in step S132, using the positional data obtained by the structured light scanner 62, various feature points or fiducials are detected within the structured light scanner data, such as fissures, ligament attachments, adhesions "A," the surface height of the patient's "P" lungs "L," or any other suitable feature point located within the thoracic cavity (FIG. 5). Once the feature points are identified, the offset of these detected feature points relative to corresponding feature points in the CLM is calculated in step S134. It is contemplated that the offset of the feature points between the structured light scanner data and the CLM data may be calculated using any suitable feature matching algorithm, such as Scale-Invariant Feature Transform (SIFT), Rotation-Invariant Feature Transform (RIFT), Generalized Robust Invariant Feature (G-RIF), Speeded Up robust Features (SURF), Principal Component Analysis SIFT (PCA-SIFT), Gradient Location-Orientation Histogram (GLOH), Gauss-SIFT, or the like.

The offsets calculated in step S134 are applied as explicit displacements through the FEA program to the CLM. The remaining mesh points are then recalculated to include these new positions and in step S136, the CLM is regenerated using the new positions to more accurately reflect the observed condition of the patient's collapsed lung "L." It is contemplated that the regenerated CLM may be selectively overlaid with the clinician's actual view of the patient's "P" lung surface displayed on the display associated with the computer 10 or the monitoring equipment 30 (FIG. 1) such that the area of interest "AOI" and the various structures within the lung "L" may be superimposed on the clinician's real-time view of the patient's lung surface, allowing the clinician to more accurately treat the area of interest "AOI."

Figure 9:
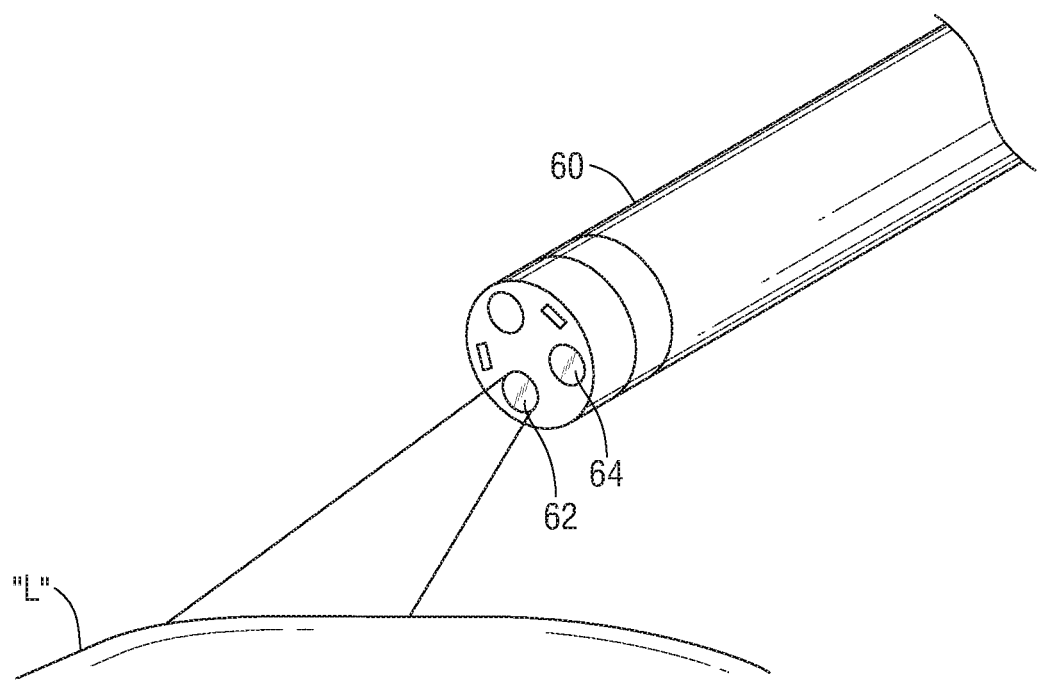
FIG. 9 is a perspective view of a thoracoscope provided in accordance with the present disclosure having a structured light scanner disposed thereon.

In another embodiment, it is contemplated that the elastic properties that are assigned to the various structures of the lung "L" may be modified and the CLM recalculated in order to obtain a better match between the CLM and the scan obtained by the structured light scanner 62 (FIG. 9). As can be appreciated, the CLM may be recalculated using an automated process or automatic optimization algorithm to loop between modification of the elastic properties, calculation of the CLM, and comparing the recalculated CLM to the scan obtained by the structured light scanner 62.

Figure 10:
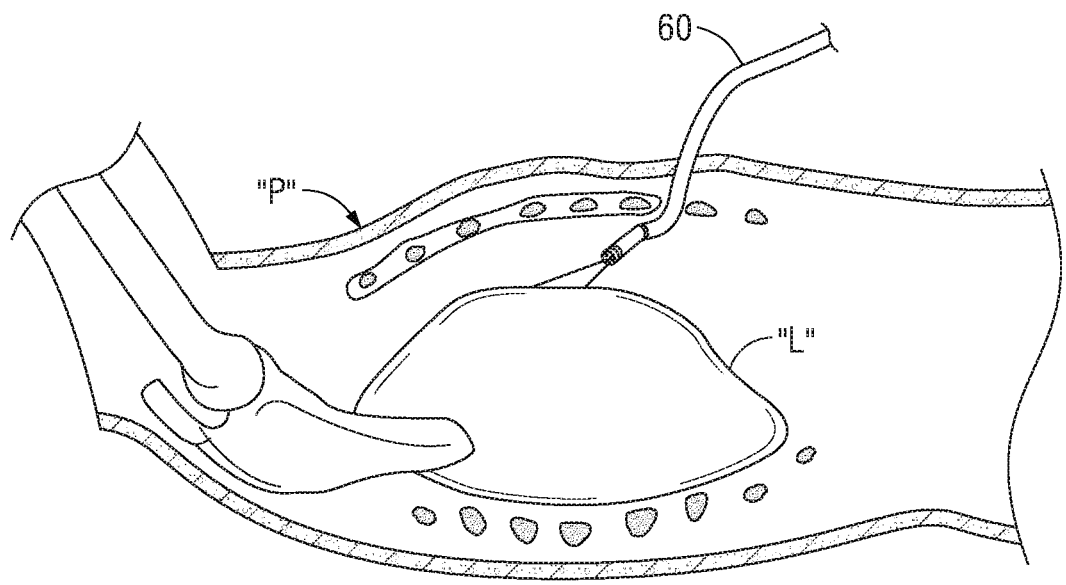
FIG. 10 is a side, cross-sectional view of the patient's thoracic cavity showing the thoracoscope of FIG. 9 advanced therein.

It is further contemplated that rather than comparing the CLM to the scan obtained by the structured light scanner 62, the CLM may be compared to the clinician's real-time view of the collapsed lung obtained by the thoracoscope 60 (FIG. 10). With this in mind, the thoracoscope 60 may include a camera (not shown) or other suitable device for capturing video images. As can be appreciated, the thoracoscope 60 may be any thoracoscope suitable for use during a video-assisted thoracoscopic surgical (VATS) procedure or image guided VATS (iVATS) procedure. For a detailed description of an exemplary thoracoscope, reference can be made to U.S. Provisional Patent Application No. 62/154,958 filed Mar. 31, 2016, entitled THORACIC ENDOSCOPE FOR SURFACE SCANNING to Sartor et al., incorporated by reference hereinabove.

Figure 11:
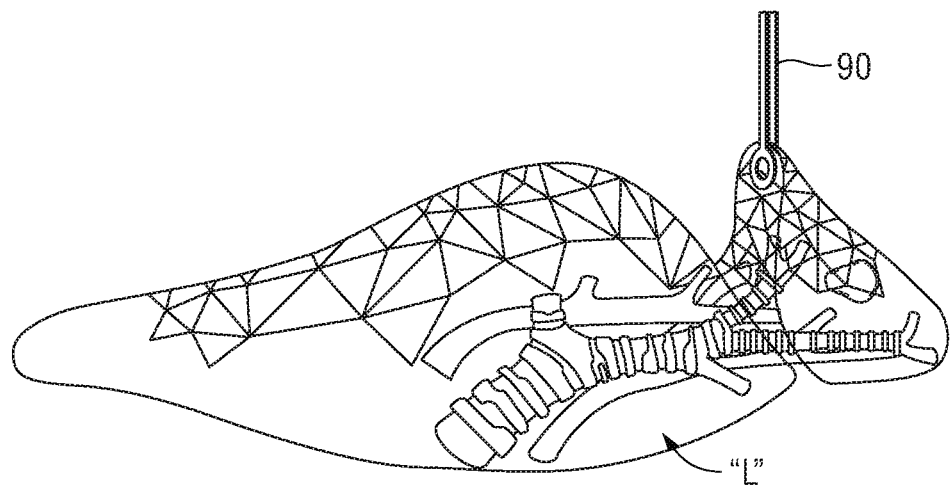
FIG. 11 is a cross-sectional view of real-time view of the patient's lungs being manipulated by a surgical instrument, showing the 3-D model superimposed over the real-time view.

As the thoracoscope 60 (FIG. 10) is advanced within the thoracic cavity, video images are captured and transmitted to the display associated with the computer 10 or the monitoring equipment 30 (FIG. 1), providing a real time view of the patient's collapsed lung "L." The 3-D model of the collapsed lung generated in step S118 is then superimposed over the real-time view of the lungs "L," such that the lesion and other structures inside the lungs "L" are illustrated in the real-time view to enable the clinician to more accurately treat the area of interest "AOI" and avoid critical structures located within the lungs "L." It is further contemplated that the CLM can reflect manipulation of the lungs "L" by the clinician. As illustrated in FIG. 11, as the clinician manipulates a portion of the lungs "L" using any suitable surgical instrument 90, such as surgical forceps or the like, the CLM may be updated to reflect the current position of the lungs "L" within the thoracic cavity. In this manner, the location of the structures within the lungs "L" and the area of interest "AOI" may be updated to reflect their true location based upon how the lungs "L" have been manipulated by the clinician. As can be appreciated, the method of regenerating the CLM described hereinabove may be applied to update the CLM as is necessary.

As noted hereinabove, VATS or iVATS may be utilized to navigate the surgical tool 80 (FIG. 12) to the area of interest "AOI." However, it is also contemplated that an electromagnetic navigation system may be utilized to guide the surgical tool 80 through the thoracic cavity and/or lungs "L" of the patient "P." In this manner, the clinician can track the location of the surgical tool 80 within the patient "P" using the electromagnetic navigation system in step S138. In order to track the location of the surgical tool 80 within the thoracic cavity, it is envisioned that a distal portion of the surgical tool 80 may include a sensor 80a (FIG. 12) disposed thereon capable of being tracked using a tracking module 112, reference sensors 114, and a transmitter mat 116 (FIG. 1). With reference again to FIG. 1, the system 100 including a navigation system capable of guiding the surgical tool 80 within the thoracic cavity and the patient's "P" lungs "L" to the area of interest "AOI" is illustrated. Patient "P" is shown lying on the operating table 40 with the surgical tool 80 advanced within the thoracic cavity using any suitable surgical device capable of permitting a surgical instrument to pass through a patient's "P" chest, such as an access port, trocar, or the like (not shown).

The navigation system may be a six degree-of-freedom electromagnetic tracking system 110, e.g., similar to those disclosed in U.S. patent application Ser. No. 14/753,288 to Brown et al. entitled "System and Method for Navigating within the Lung," filed Jun. 29, 2015 and published PCT Application Nos. WO 00/10456 and WO 01/67035, the entire content of each of which is incorporated herein by reference, or another suitable positioning measuring system, is utilized for performing registration and navigation, although other configurations are also contemplated. Tracking system 110 includes tracking module 112, a plurality of reference sensors 114, and a transmitter mat 116. The tracking system 110 is configured for use with the surgical tool 80 having the sensor 80a disposed at a distal portion thereof that enables monitoring of the position and orientation of the distal portion of the surgical tool 80, in six degrees of freedom, relative to the reference coordinate system. For a detailed description of the construct of exemplary navigation systems, reference can be made to U.S. Patent Application Publication No. 2015/0265257 to Costello et al. entitled "Systems, and Methods for Navigating a Biopsy Tool to a Target Location and Obtaining a Tissue Sample Using the Same," filed Dec. 9, 2014, the entire content of which is incorporated by reference herein.

The transmitter mat 116 is positioned beneath the patient "P" and is a transmitter of electromagnetic radiation and includes a stack of three substantially planar rectangular loop antennas (not shown) configured to be connected to drive circuitry (not shown). For a detailed description of the construction of exemplary transmitter mats, which may also be referred to as location boards, reference may be made to U.S. Patent Application Publication No. 2009/0284255 to Zur entitled "Magnetic Interference Detection System and Method," filed Apr. 2, 2009, the entire contents of which is incorporated by reference herein.

The transmitter mat 116 and the plurality of reference sensors 114 are interconnected with tracking module 112, which derives the location of each sensor 114 in six degrees of freedom. One or more of the reference sensors 114 are attached to the chest of the patient "P." The six degrees of freedom coordinates of the reference sensors 114 are sent to the computer 10 (which includes the appropriate software) where they are used to calculate a patient coordinate frame of reference. Registration is generally performed by identifying locations in both the 3-D model and the patient's "P" thoracic cavity and/or lungs "L" and measuring the coordinates in both systems. These coordinates are then correlated and the two coordinate systems are aligned.

In use, the surgical tool 80 is advanced within the thoracic cavity of the patient "P." Automatic registration is performed by moving the surgical tool 80 through the thoracic cavity. More specifically, data pertaining to locations of the sensor 80a while the surgical tool 80 is moving through the thoracic cavity is recorded using the tracking module 112, the reference sensors 114, and the transmitter mat 116. A shape resulting from this location data is compared to an interior geometry of the thoracic cavity and/or lungs "L" of the 3-D model generated using the methods described hereinabove, and a location correlation between the shape and the 3-D model based on the comparison is determined, e.g., utilizing the software on computer 10. It is contemplated that the location of the distal portion of the surgical tool may be displayed on the 3-D model or CLM such that the clinician may identify the position of the surgical tool 80 within the thoracic cavity and/or lungs "L" of the patient "P."

Referring again to FIG. 1, system 100 may be utilized to navigate the surgical tool 80 through the thoracic cavity and within the patient's "P" lungs "L" to the area of interest "AOI." To facilitate such navigation, the computer 10, the monitoring equipment 30, and/or any other suitable display may be configure to display the CLM including the selected pathway from the current location of the sensor 80a of the surgical tool 80 to the area of interest "AOI." Navigation of the surgical tool 80 to the area of interest "AOI" using the tracking system 110 is similar to that detailed above and thus, is not detailed here for purposes of brevity.

Once the surgical tool 80 has been successfully navigated to the area of interest "AOI," the clinician may remove or otherwise treat the area of interest "AOI" using the surgical tool 80. For a detailed description of exemplary planning and navigation of a surgical tool, reference may be made to U.S. patent application Ser. No. 14/753,288 to Brown et al., previously incorporated by reference herein.

The electromagnetic waves generated by the transmitter mat 116 are received by the various sensor elements configured for use with the surgical tool 80, and are converted into electrical signals that a sensed via the reference sensors 114. The tracking system 110 further includes reception circuitry (not shown) that has appropriate amplifiers and A/D converters that are utilized to receive the electrical signals from the reference sensors 114 and process these signals to determine and record location data of the sensor assembly. The computer 10 may be configured to receive the location data from the tracking system 110 and display the current location of the sensor assembly on the CLM and relative to the selected pathway generated during the planning phase, e.g., on the computer 10, the monitoring equipment 30, or other suitable display. Thus, navigation of the surgical tool 80 to the area of interest "AOI" and/or manipulation of the surgical tool 80 relative to the area of interest "AOI," as detailed above, can be readily achieved.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

What is claimed is:

1. A method of modeling lungs of a patient, comprising:
    acquiring computer tomography (CT) data of a patient's lungs;
    storing a software application within a memory associated with a computer, the computer having a processor configured to execute the software application; and
    executing the software application to:
        differentiate tissue located within the patient's lungs using the acquired CT data;
        generate a three-dimensional (3-D) model of the patient's lungs based on the acquired CT data and the differentiated tissue;
        apply a material property to each tissue of the differentiated tissue within the generated 3-D model;
        generate a mesh of the generated 3-D model;
        generate a constraint using a shell surface offset from a surface of the patient's lungs to create a boundary condition;
        calculate a displacement of the patient's lungs in a collapsed state based on the constraint, the material property applied to the differentiated tissue, and the mesh; and
        generate a collapsed lung model of the patient's lungs based on the calculated displacement of the patient's lungs.

2. The method of claim 1, wherein executing the software application to differentiate tissue located within the patient's lungs includes executing the software application to group similar types of tissue based on a corresponding contrast density associated with the tissue.

3. The method of claim 1, wherein executing the software application to differentiate tissue within the patient's lungs includes executing the software application to identify low contrast density tissue and high contrast density tissue.

4. The method of claim 3, wherein executing the software application to identify low contrast density tissue includes executing the software application to identify at least one structure from the group consisting of lung parenchyma, pleura fissure lines, and bronchi.

5. The method of claim 3, wherein executing the software application to identify high contrast density tissue includes executing the software application to identify at least one structure from the group consisting of luminal structures, hilar structures, and bronchopulmonary lymph nodes.

6. The method of claim 3, further comprising executing the software application to:
    select a contrast density tissue from the low contrast density tissue and the high contrast density tissue; and
    generate an additional offset shell surface to represent structures adjacent to the patient's lungs based on the selected contrast density tissue.

7. The method of claim 1, further comprising executing the software application to apply a stiffness or an elasticity property to the shell surface offset from the surface of the patient's lungs.

8. The method of claim 1, further comprising executing the software application to apply a directional effect of gravity to the generated 3-D model.

9. The method of claim 1, further comprising executing the software application to:
    calculate a curvature of the patient's spine in a coronal plane; and
    calculate a reduction in lung volume based on the calculated curvature of the patient's spine.

10. The method of claim 9, further comprising executing the software application to alter the generated 3-D model to reflect the calculated reduction in lung volume.

11. The method of claim 1, further comprising executing the software application to:
    identify adhesions within a thoracic cavity of the patient; and
    display the 3-D model of the patient's lungs as sitting higher in the patient's thoracic cavity than the patient's lungs actually sit in the patient's thoracic cavity based on the identified adhesions.

12. A method of modeling lungs of a patient, comprising:
    segmenting anatomical features shown in computer tomography (CT) data of a patient's lungs;
    generating a three-dimensional (3-D) model of the patient's lungs based on the CT data and the segmented anatomical features;
    applying a material property to each segmented anatomical feature within the 3-D model;
    generating a mesh of the 3-D model;
    generating a constraint using a shell surface offset from a surface of the patient's lungs to create a boundary condition;
    calculating a displacement of the patient's lungs in a collapsed state based on the constraint, the material property applied to each segmented anatomical feature and the mesh; and
    generating a collapsed lung model of the patient's lungs based on the calculated displacement of the patient's lungs.

13. The method of claim 12, further comprising applying a smoothing algorithm to the 3-D model.

14. The method of claim 13, further comprising applying a secondary smoothing algorithm to the 3-D model.

15. The method of claim 13, further comprising rotating the 3-D model to a lateral decubitus position.

* * * * *